US009034013B2

United States Patent
Sengun

(10) Patent No.: US 9,034,013 B2
(45) Date of Patent: May 19, 2015

(54) SYSTEMS, DEVICES, AND METHODS FOR SECURING TISSUE USING A SUTURE HAVING ONE OR MORE PROTRUSIONS

(71) Applicant: Medos International Sarl, Le Locle (CH)

(72) Inventor: Mehmet Ziya Sengun, Canton, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 0 days.

(21) Appl. No.: 14/522,562

(22) Filed: Oct. 23, 2014

(65) Prior Publication Data
US 2015/0045832 A1 Feb. 12, 2015

Related U.S. Application Data

(62) Division of application No. 13/465,362, filed on May 7, 2012, now Pat. No. 8,894,684.

(51) Int. Cl.
*A61B 17/04* (2006.01)
*A61L 17/00* (2006.01)

(52) U.S. Cl.
CPC ..... *A61B 17/0401* (2013.01); *A61B 2017/0496* (2013.01)

(58) Field of Classification Search
CPC ............ A61B 17/0401; A61B 2017/0409; A61B 17/0469; A61B 2017/0477; A61B 2017/0464; A61B 2017/0496
USPC .......... 606/144–148, 151, 228–232
See application file for complete search history.

(56) References Cited

U.S. PATENT DOCUMENTS

| 2,566,625 A | 9/1951 | Nagelmann |
| 2,600,395 A | 6/1952 | Domoj et al. |
| 2,697,624 A | 12/1954 | Thomas et al. |

(Continued)

FOREIGN PATENT DOCUMENTS

| AU | 2008229746 A1 | 10/2008 |
| CA | 2772500 A1 | 9/2013 |

(Continued)

OTHER PUBLICATIONS

[No Author Listed] Arthroscopic Knot Tying Manual 2005. DePuy Mitek.

(Continued)

*Primary Examiner* — Katherine M Shi

(57) ABSTRACT

Systems, devices, and methods are provided for securing soft tissue to bone. One exemplary embodiment of a surgical repair construct includes an anchor, a filament having a snare on one end and a collapsible loop on another end, and a suture having a plurality of stationary protrusions. The suture is configured to be coupled to detached tissue and have its ends passed through an opening in the snare. The snare can be collapsed around the suture so at least one of the protrusions is proximal of the collapsed snare. The anchor can be disposed in bone and the filament coupled thereto. Accordingly, collapsing the snare around the suture couples the tissue to bone, and applying tension to a tensioning limb of the filament can collapse the loop to incrementally tighten and secure the tissue to bone. Other exemplary systems, devices, and methods for use with tissue repair are also provided.

8 Claims, 4 Drawing Sheets

(56) References Cited

U.S. PATENT DOCUMENTS

| | | |
|---|---|---|
| 2,758,858 A | 8/1956 | Smith |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker |
| 5,645,850 A | 7/1997 | Bezwada et al. |
| 5,647,616 A | 7/1997 | Hamilton |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,319,271 B1 | 11/2001 | Schwartz |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,716,234 B2 | 4/2004 | Grafton et al. |
| 6,767,037 B2 | 7/2004 | Wenstrom, Jr. |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,905,904 B2 | 3/2011 | Stone et al. |
| 7,959,650 B2 | 6/2011 | Kaiser et al. |
| 7,981,140 B2 | 7/2011 | Burkhart |
| 8,012,171 B2 | 9/2011 | Schmieding |
| 8,088,146 B2 | 1/2012 | Wert et al. |
| 8,118,836 B2 | 2/2012 | Denham et al. |
| 8,137,382 B2 | 3/2012 | Denham et al. |
| 8,231,653 B2 | 7/2012 | Dreyfuss |
| 8,231,654 B2 | 7/2012 | Kaiser et al. |

(56) References Cited

U.S. PATENT DOCUMENTS

| | | |
|---|---|---|
| 8,419,769 B2 | 4/2013 | Thal |
| 8,790,370 B2 | 7/2014 | Spenciner et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,894,684 B2 | 11/2014 | Sengun |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0236373 A1 | 11/2004 | Anspach |
| 2005/0033363 A1 | 2/2005 | Bojarski et al. |
| 2005/0119696 A1 | 6/2005 | Walters et al. |
| 2005/0137624 A1 | 6/2005 | Fallman |
| 2005/0187577 A1 | 8/2005 | Selvitelli et al. |
| 2005/0251208 A1 | 11/2005 | Elmer et al. |
| 2006/0106423 A1 | 5/2006 | Weisel et al. |
| 2006/0178680 A1 | 8/2006 | Nelson et al. |
| 2006/0178702 A1 | 8/2006 | Pierce et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1 | 3/2007 | Dreyfuss |
| 2007/0083236 A1 | 4/2007 | Sikora et al. |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0239209 A1 | 10/2007 | Fallman |
| 2008/0009901 A1 | 1/2008 | Redmond et al. |
| 2008/0009904 A1 | 1/2008 | Bourque et al. |
| 2008/0027446 A1 | 1/2008 | Stone et al. |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208265 A1 | 8/2008 | Frazier et al. |
| 2008/0228265 A1 | 9/2008 | Spence et al. |
| 2008/0255613 A1 | 10/2008 | Kaiser et al. |
| 2008/0275469 A1 | 11/2008 | Fanton et al. |
| 2008/0312689 A1 | 12/2008 | Denham et al. |
| 2009/0023984 A1 | 1/2009 | Stokes et al. |
| 2009/0036905 A1 | 2/2009 | Schmieding |
| 2009/0054928 A1 | 2/2009 | Denham et al. |
| 2009/0062850 A1 | 3/2009 | Ken |
| 2009/0062854 A1 | 3/2009 | Kaiser et al. |
| 2009/0082805 A1 | 3/2009 | Kaiser et al. |
| 2009/0082807 A1 | 3/2009 | Miller et al. |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0281568 A1 | 11/2009 | Cendan et al. |
| 2009/0281581 A1 | 11/2009 | Berg |
| 2009/0287246 A1 | 11/2009 | Cauldwell et al. |
| 2009/0306711 A1 | 12/2009 | Stone et al. |
| 2009/0312776 A1 | 12/2009 | Kaiser et al. |
| 2009/0312794 A1 | 12/2009 | Nason et al. |
| 2009/0318958 A1 | 12/2009 | Ochiai |
| 2010/0004683 A1 | 1/2010 | Hoof et al. |
| 2010/0016892 A1 | 1/2010 | Kaiser et al. |
| 2010/0094425 A1 | 4/2010 | Bentley et al. |
| 2010/0162882 A1 | 7/2010 | Shakespeare |
| 2010/0204730 A1 | 8/2010 | Maiorino et al. |
| 2010/0249809 A1 | 9/2010 | Singhatat et al. |
| 2010/0249834 A1 | 9/2010 | Dreyfuss |
| 2010/0256677 A1 | 10/2010 | Albertorio et al. |
| 2010/0292732 A1 | 11/2010 | Hirotsuka et al. |
| 2010/0292792 A1 | 11/2010 | Stone et al. |
| 2011/0022083 A1 | 1/2011 | DiMatteo et al. |
| 2011/0077667 A1 | 3/2011 | Singhatat et al. |
| 2011/0190815 A1 | 8/2011 | Saliman |
| 2011/0208240 A1 | 8/2011 | Stone et al. |
| 2011/0213416 A1 | 9/2011 | Kaiser |
| 2011/0238111 A1 | 9/2011 | Frank |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0101523 A1 | 4/2012 | Wert et al. |
| 2012/0130423 A1 | 5/2012 | Sengun et al. |
| 2012/0130424 A1 | 5/2012 | Sengun et al. |
| 2012/0150223 A1 | 6/2012 | Manos et al. |
| 2012/0165864 A1 | 6/2012 | Hernandez et al. |
| 2012/0179199 A1 | 7/2012 | Hernandez et al. |
| 2012/0253389 A1 | 10/2012 | Sengun et al. |
| 2012/0253390 A1 | 10/2012 | Sengun |
| 2012/0296375 A1 | 11/2012 | Thal |
| 2013/0110165 A1 | 5/2013 | Burkhart et al. |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2013/0296934 A1 | 11/2013 | Sengun |
| 2014/0081324 A1 | 3/2014 | Sengun |
| 2014/0188163 A1 | 7/2014 | Sengun |
| 2014/0188164 A1 | 7/2014 | Sengun |
| 2014/0277132 A1 | 9/2014 | Sengun |
| 2014/0330312 A1 | 11/2014 | Spenciner et al. |
| 2014/0343606 A1 | 11/2014 | Hernandez et al. |
| 2014/0343607 A1 | 11/2014 | Sengun et al. |
| 2015/0012038 A1 | 1/2015 | Sengun et al. |

FOREIGN PATENT DOCUMENTS

| | | |
|---|---|---|
| EP | 0870471 A1 | 10/1998 |
| EP | 1 199 035 A1 | 4/2002 |
| EP | 1 707 127 A1 | 10/2006 |
| EP | 2 277 457 A1 | 1/2011 |
| EP | 2 455 003 A2 | 5/2012 |
| EP | 2 572 650 A1 | 3/2013 |
| WO | 95/19139 A1 | 7/1995 |
| WO | 97/17901 A1 | 5/1997 |
| WO | 98/11825 A1 | 3/1998 |
| WO | 01/06933 A2 | 2/2001 |
| WO | 03/022161 A2 | 3/2003 |
| WO | 2007/109769 A1 | 9/2007 |

OTHER PUBLICATIONS

[No Author Listed] Gryphon Brochure. DePuy Mitek. 2 pages (undated).

[No Author Listed] Versalok Anchor. Brochure. DePuy Mitek, a Johnson & Johnson company, 92 pages, 2007.

Allock, The Encyclopedia of Polymer Science, vol. 13, pp. 31-41, Wiley Intersciences, John Wiley & Sons, 1988.

Cohn et al., Biodegradable PEO/PLA block copolymers. J Biomed Mater Res. Nov. 1988;22(11):993-1009.

Cohn et al., Polym Preprint. 1989;30(1):498.

Dahl et al., Biomechanical characteristics of 9 arthroscopic knots. Arthroscopy. Jun. 2010;26(6):813-8.

EP Search Report for Application No. 11190157.5 issued Feb. 27, 2012. (8 pages).

EP Search Report for Application No. 11190159.1 issued Feb. 21, 2012. (8 pages).

Extended European Search Report for Application No. 11190157.5 issued Jul. 6, 2012. (10 pages).

(56) References Cited

OTHER PUBLICATIONS

Extended European Search Report for Application No. 11190159.1 issued Jul. 6, 2012. (11 pages).
Extended European Search Report for Application No. 13166905.3 issued Aug. 13, 2013 (9 Pages).
Extended European Search Report for Application No. 13166907.9, issued Aug. 1, 2013 (6 pages).
Extended European Search Report for Application No. 13166908.7, issued Aug. 23, 2013 (8 pages).
Extended European Search Report for Application No. 13185425.9 issued Dec. 16, 2013 (9 Pages).
Extended European Search Report for Application No. 13199724.9 issued Apr. 4, 2014 (6 Pages).
Extended European Search Report for Application No. 11195100.0 issued Oct. 17, 2012. (7 pages).
Heller, Handbook of Biodegradable Polymers, edited by Domb, et al., Hardwood Academic Press, pp. 99-118 (1997).
International Search Report for Application No. PCT/US2011/067119, mailed Jun. 4, 2012. (6 pages).
Kemnitzer et al., Handbook of biodegradable Polymers. Eds. Domb et al. Hardwood Acad. Press. 1997;251-72.
Vandorpe et al., Handbook of Biodegradable Polymers, edited by Domb, et al., Hardwood Acad. Press, pp. 161-182 (1997).

SYSTEMS, DEVICES, AND METHODS FOR SECURING TISSUE USING A SUTURE HAVING ONE OR MORE PROTRUSIONS

CROSS REFERENCE TO RELATED APPLICATIONS

The present application is a divisional of U.S. patent application Ser. No. 13/465,362, filed May 7, 2012, and entitled "SYSTEMS, DEVICES, AND METHODS FOR SECURING TISSUE USING A SUTURE HAVING ONE OR MORE PROTRUSIONS," which is hereby incorporated by reference in its entirety.

FIELD

The present disclosure relates to systems, devices, and methods for securing soft tissue to bone, and more particularly relates to securing soft tissue using a suture having one or more protrusions formed thereon while minimizing or eliminating the tying of knots to tension and secure the tissue.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to soft and weak bones leading to inadequate suture-to-anchor fixation.

Arthroscopic knot tying is commonly practiced in shoulder rotator cuff and instability procedures. Typically, an anchor loaded with suture is first attached to bone. The suture is normally slidably attached to the anchor through an eyelet or around a post, such that a single length of suture has two free limbs. One limb of the suture is passed through soft tissue to be repaired such as a tendon or labrum. The two ends of the suture are then tied to each other, thereby capturing the soft tissue in a loop with the anchor. Upon tightening the loop, the soft tissue is approximated to the bone via the anchor.

Surgeons typically tie the suture ends using a surgical sliding knot such as the Tennessee Slider or Duncan Loop. After advancing the knot distally to tighten the loop, a number of additional half hitches or other knots are tied in an effort to secure the new location of the sliding knot. The additional knots are needed because a conventional sliding knot used in current repair constructs does not provide the necessary protection against loosening or slippage, especially when tension is placed primarily on the limbs of the loop. The generally accepted practice is to follow the sliding knot with at least three reversed half hitches on alternating posts of the suture.

Before one or more half hitches or other knots can be added to the sliding knot, however, there exists a potential for the sliding knot to slip, that is, for the loop to enlarge as the tissue places tension on the loop. This has been referred to as "loop security" and can reportedly occur even in the hands of very experienced surgeons. Sometimes, even fully-tied knots may slip. In addition to this "loop security" problem, conventional knots typically have an overall size that can be obstructive or intrusive, especially in tight joints, which may damage cartilage or other tissue by abrasion with the knot.

Suture anchor systems with sliding and locking knots for repairing torn or damaged tissue include U.S. Pat. No. 6,767,037 by Wenstrom, Jr. Other suture anchor systems suited especially for meniscal repair are disclosed in U.S. Pat. No. 7,390,332 by Selvitelli et al. and are utilized in the OmniSpan™ meniscal repair system commercially available from DePuy Mitek Inc., 325 Paramount Drive, Raynham, Mass. 02767. Screw-type anchors normally require anchor attachment before operating sutures, which can lead to challenges related to the connection between the suture and the tissue.

There are a number of suture implant systems which proclaim to be "knotless," that is, to not require a surgeon to tie a knot during surgery. Many such systems control tension on tissue by the depth to which an anchor is driven into bone. U.S. Pat. Nos. 5,782,864 and 7,381,213 by Lizardi disclose certain types of suture anchors that capture a fixed-length loop of suture. Adjustable loop knotless anchor assemblies utilizing an anchor element inserted into a sleeve are described by Thal in U.S. Pat. Nos. 5,569,306 and 6,045,574 and in U.S. Patent Application Publication No. 2009/0138042. Other systems having clamps or other locking mechanisms include U.S. Pat. No. 5,702,397 by Goble et al. and U.S. Patent Application Publication No. 2008/0091237 by Schwartz et al. Present, so-called "knotless" designs, however, generally suffer from inadequate suture-to-anchor fixation and/or inadequate anchor-to-bone fixation, among other deficiencies.

It is therefore desirable to provide systems, devices, and methods for use in soft tissue repair that are robust, strong, and improve "loop security," yet minimize or eliminate the number and size of knots to be tied by a surgeon, particularly during arthroscopic repair procedures.

SUMMARY

Systems, devices, and methods are generally provided for securing soft tissue to bone. In one exemplary embodiment a surgical repair construct includes an anchor, a filament having a collapsible snare formed on one end thereof and a collapsible loop at a second end thereof, and a suture having a plurality of stationary protrusions formed thereon in a spaced-apart arrangement. The anchor can include a filament engagement feature and can be capable of being fixated in bone. The filament and the suture are both capable of being passed through soft tissue to be repaired. An opening of the filament's snare can be configured to receive the suture such that the snare is slidable with respect to the suture and collapsible around the suture. The filament's collapsible loop can be coupled to the anchor's filament engagement feature, and the loop can include a sliding knot with a tensioning limb extending therefrom. The tensioning limb can be effective to collapse the collapsible loop independent of the snare. Further, the collapsible loop can be capable of being tightened incrementally to secure the soft tissue to bone.

The snare can have a variety of configurations and can be made in a number of different ways. In some embodiments, the snare can be configured by passing a terminal end of the filament through an adjacent portion of the filament. The terminal end can include a protrusion that maintains the terminal end within the portion of the filament through which it is disposed. In some other embodiments, the snare can be configured by a second sliding knot that is effective to collapse the snare. In still other embodiments, the snare can include a coaxial sliding neck that is effective to collapse the snare. Further, a flexible member can be removably placed in a portion of the snare to prevent unintentional collapse of the snare, and when the snare includes a coaxial sliding neck, the flexible member can be removably disposed therethrough to immobilize the coaxial sliding neck. The filament can be a cannulated surgical filament or a braided suture filament. Further, in embodiments that include a flexible member, the flexible member can be formed of a second filament. A thickness of the second filament can be in the range of about 25 gauge to about 40 gauge, while a thickness of either or both of the filament that forms the collapsible loop and the collapsible snare can be in the range of about 20 gauge to about 34 gauge. The diameter of the protrusions of the suture can be in the range of about 0.5 millimeters to about 2 millimeters.

In one exemplary embodiment of a surgical repair method, the method includes passing a first end of a suture having formed thereon a plurality of stationary protrusions through and/or into tissue. The first end of the suture can be passed through the tissue such that first and second limbs of the suture extend from the first side of the tissue. The suture can be arranged in the tissue such that at least one of the protrusions is disposed adjacent to at least one of the first and second sides of the tissue. In one embodiment at least one protrusion is disposed adjacent to the first side of the tissue. The method can also include inserting an anchor into bone in proximity to the detached soft tissue. The anchor can have a filament engagement feature to which a filament is attached, and the filament can have a collapsible snare formed on one end and a collapsible loop at its second end, the collapsible loop being coupled to the filament engagement feature. The collapsible loop can include a sliding knot with a tensioning limb that extends therefrom, and the tensioning limb can be effective to collapse the collapsible loop independent of the snare. The method can further include inserting the first and second limbs of the suture through an opening formed in the snare, sliding the snare distally towards the tissue and distally past at least one protrusion disposed on the first side of the tissue, collapsing the snare around the first and second limbs of the suture, and pulling the snare towards the anchor by shortening the collapsible loop and thus drawing the tissue into proximity with the bone.

In some embodiments the step of pulling the snare towards the anchor by shortening the collapsible loop can include tensioning the tensioning limb. In such embodiments the snare can be advanced in an incremental fashion without slackening of the filament. The suture can include at least four protrusions. In some embodiments the snare can be positioned between at least one protrusion and the tissue, while in some other embodiments the snare can be positioned between at least two protrusions and the tissue. Optionally, a flexible member can be disposed in a portion of the snare to prevent unintentional collapse thereof. In such embodiments the flexible member can be removed from the snare prior to collapsing the snare. The methods provided for herein can be performed without tying a knot.

BRIEF DESCRIPTION OF DRAWINGS

This invention will be more fully understood from the following detailed description taken in conjunction with the accompanying drawings, in which.

DETAILED DESCRIPTION

Figure 1:
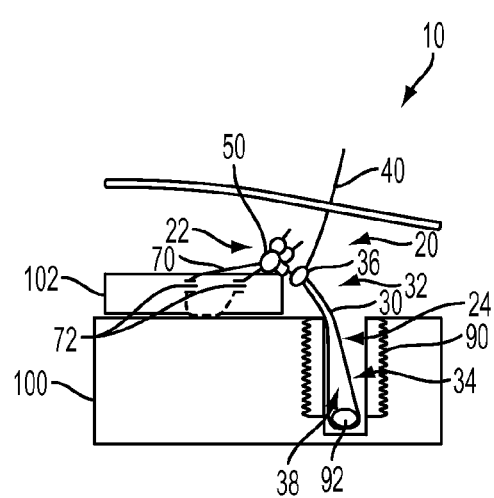
FIG. 1 is schematic view of one exemplary embodiment of a surgical repair construct disposed at a surgical site.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction a component can be tensioned or pulled, these arrows are illustrative and in no way limit the direction the respective component can be moved. A person skilled in the art will recognize other ways and directions for creating the desired result. Additionally, a number of terms may be used throughout the disclosure interchangeably but will be understood by a person skilled in the art.

Systems, devices, and methods for soft tissue repair are generally provided and they generally involve the use of surgical filaments and sutures that are configured in a variety of manners to minimize and/or eliminate the tying of knots during a surgical procedure. The systems and devices described herein provide superior strength for use in a number of different surgical procedures, such as rotator cuff and instability repair procedures and other types of tendon and tissue repair procedures. The systems and devices provided herein also allow for both improved and new procedures for soft tissue repair. For example, the systems and devices provided herein can be used to advance tissue towards bone in an incremental fashion without the construct backlashing. Reducing and/or eliminating backlashing during advancement can prevent the size of the collapsible loop from increasing and prevent the tissue from moving away from the bone and/or not being held tightly in place with respect to the bone due to backlashing. Additionally, the systems and devices allow a surgeon to secure a location of the tissue without tying a knot during the procedure.

As shown by one exemplary embodiment of a surgical repair construct 10 in FIG. 1, the constructs of the present disclosure generally include a filament 20 that forms a snare 50 at a first end 22 thereof and a collapsible loop 30 at a second end 24 thereof, a suture 70 having one or more stationary protrusions 72 formed therein, and an anchor 90 coupled to the collapsible loop 30, for instance at an engagement feature 92 of the anchor 90. In the illustrated embodiment, the anchor 90 is disposed in bone 100, the suture 70 is passed through soft tissue, for example tendon 102, and the snare 50 is slidable with respect to the suture 70 and collapsed around a portion of the suture 70 to couple the bone 100 and tendon 102 via the surgical repair construct 10. As will be described in greater detail below, the snare 50 can begin outside of the body and be moved distally (e.g., towards the bone 100) such that it is distal of at least one of the protrusions 72. The snare 50 can subsequently be collapsed such that the protrusions 72 prevent the snare 50 from backlashing in a proximal direction (e.g., away from the bone 100), which would allow the tissue to move away from the bone. The filament 20 can further include a sliding knot 36 at a first end 32 of the loop 30, which can be moved distally towards a second end 34 of the loop 30 to collapse a size of an opening 38 formed by the loop 30, thereby applying a force to draw the tendon 102 towards the bone 100. A collapsible tail or tensioning limb 40 can extend from the sliding knot 36 and can be operable to move the sliding knot 36 towards the second end 34 in a ratchet-like or incremental manner to secure the tendon 102 to the bone 100. Movement, of the snare 50, including collapsing the snare 50, and movement of the collapsible loop 30, including by tensioning the tensioning limb 40, can be independent of each other.

Filaments for use in a surgical repair construct can have a variety of configurations, some of which are described in greater detail below. Generally filaments have a portion for grasping a separate suture coupled to tissue, illustrated herein as a snare, and a portion, illustrated herein as a collapsible loop, that is coupled to bone and to which tension can be applied to draw the tissue towards bone. In operation, grasping the separate suture couples the tissue to the filament and collapsing the loop towards the bone draws the tissue towards the bone.

Figure 2:
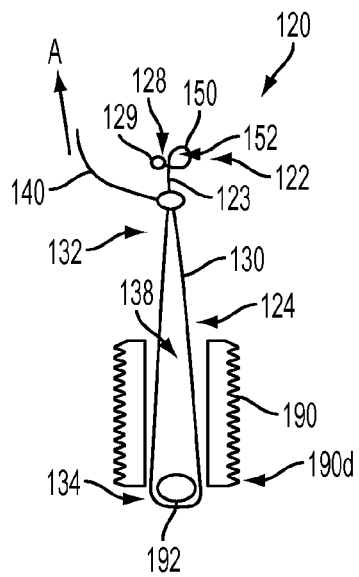
FIG. 2 is a schematic view of one exemplary embodiment of a filament coupled to an anchor for use as part of a surgical repair construct.

FIG. 2 provides one exemplary embodiment of a filament 120 for use as part of a surgical repair construct. A first end 122 of the filament 120 can include a snare 150 that is configured to collapse under tension, a second end 124 of the filament 120 can include a collapsible loop 130 that is configured to collapse under tension, independent of the snare 150, and a neck 123 can extend between the first and second ends 122, 124. The filament 120 having both a snare 150 and a collapsible loop 130 can be referred to as a snare assembly.

The snare 150 can be formed in a variety of ways known to those skilled in the art, some of which are discussed in greater detail below. In the illustrated embodiment the snare 150 is formed by passing a portion of the filament 120 through itself. Further, a protrusion 129 can be formed at a terminal end 128 of the filament 120, proximate to the snare 150, to prevent pull-through and to resist fraying, particularly if the filament 120 is a braided filament. The protrusion 129 can be pre-formed, or it can be formed by a surgeon, for instance by tying a half-hitch or other simple knot.

Figure 3:
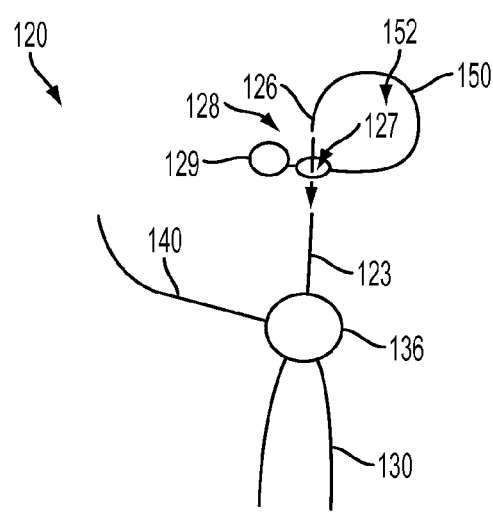
FIG. 3 is a close-up view of a portion of the filament of FIG. 2, illustrating the formation of a snare using the filament.

FIG. 3 illustrates one of the many ways the snare 150 can be formed. As shown, a leading end 126 of the filament 120 can be passed through an opening 127 of the filament 120 to form a collapsible opening 152 of the snare 150. The opening 127 can be pre-formed and collapsible, or alternatively, it can be part of the construct of the filament 120, such as an opening due to the filament 120 being braided. The leading end 126 can be used to form the other portions of the filament 120, including the collapsible loop 130, a sliding knot 136, and a tensioning limb 140, which are described in greater detail below, for instance by forming the loop 130 and the sliding knot 136 on the tensioning limb 140. In this arrangement, any tension applied on the neck 123, such as by pulling the tensioning limb 140, not only collapses the snare 150 to strangulate objects passing therethrough, but also binds the portion of the filament 120 passing through the opening 127 upon itself. In other arrangements, a half-hitch or other simple knot can be tied adjacent to the opening, and the filament 120 can be looped through that simple knot.

The loop 130 can likewise be formed in a variety of ways known to those skilled in the art, some of which are discussed in greater detail below. In the illustrated embodiment of FIG. 2, the loop 130 has first and second ends 132, 134, with a sliding knot 136 formed at the first end 132. As shown, the second end 134 can be slidably coupled to an anchor 190, for instance at an engagement feature 192 thereof, such as a saddle or post. While in the illustrated embodiment the engagement feature 192 is located at a distal end 190d of the anchor 190, it can be located in any part of the anchor 190 and it allows the filament 120 to be slidably engaged with the anchor 190.

The collapsible loop 130 can be expanded and collapsed as desired by the sliding knot 136. Accordingly, when the loop 130 is coupled to tissue, for instance by having a suture disposed through the snare 150 of the filament 120 that forms the loop 130, collapsing the loop 130 creates a force that draws the tissue towards a desired location. As shown in FIG. 2, as the sliding knot 136 is moved towards the second end 134, the loop 130 collapses, and as the knot 136 is moved away from the second end 134, the size of an opening 138 of the loop 130 increases. The sliding knot 136 can be formed in a variety of ways using a variety of techniques well known to those skilled in the art. Non-limiting examples of the types of knots that can be used as the loop's sliding knot include a Buntline Hitch, a Tennessee Slider, a Duncan Loop, a Hangman's Noose, and a loop having a coaxial sliding neck. The type of knot selected may affect the manner in which the loop 130 can be collapsed, and a person having skill in the art will recognize how to collapse the loop based on the type of knot used.

As shown in FIG. 2, the loop 130 can also have a collapsible tail or tensioning limb 140 that extends from the sliding knot 136. The tensioning limb 140 can be a terminal end of a limb of the filament 120 used to form the sliding knot 136 that completes the collapsible loop 130. The tensioning limb 140 can be operable to tension and collapse the loop 130 by moving the sliding knot 136 towards the loop second end 134.

More particularly, applying tension to the tensioning limb 140 in approximately a direction A can cause the knot 136 to slide distally towards the second end 134. As a result, the sliding knot 136 can move in a ratchet-like or incremental fashion such that the knot 136 moves towards the second end 134 with little or no backlashing, which in turn minimizes or prevents the opening 138 of the collapsible loop 130 from increasing in size. When tension is not applied, the location of the sliding knot 136 remains substantially fixed, and further tensioning of the tensioning limb 140 can cause further distal movement of the knot 136 until either the tension is released or an obstruction precludes further distal movement of the knot 136. The self-locking capabilities provided by this sliding knot 136 that results from the overall formation of a surgical repair construct including the filament 120 are beneficial at least because of the ability to incrementally advance the knot 136 with minimal or no backlashing. Still further, in some embodiments a second, stationary tail or tail can also be formed and can be used, for example, to assist in threading the filament through tissue, providing additional strength to the repair, and/or performing various surgical procedures, such as double row procedures With reference to FIG. 3, an example of steps for manufacturing the snare assembly formed by the filament 120 is as follows. The protrusion 129 can be formed at the terminal end 128 by tying a knot and a tail of a terminal end thereof can be trimmed. The leading end 126 can be looped and passed through itself at the opening 127, in close proximity to the protrusion 129, to form the opening 152 in the snare 150. Alternatively, a second half-hitch can be tied in close proximity to the protrusion 129 and the leading end 126 can be passed through the second half-hitch to form the opening 152 in the snare 150. A flexible member, such as a filament or suture (discussed in greater detail below with respect to FIGS. 6, 7A, and 7B), or other objects, including but not limited to thin mandrel or pin, can be placed through the snare 150 to maintain patency. The sliding knot 136, such as a Buntline Hitch, can be tied in close proximity to the snare 150 and the filament 120 can be placed in sliding engagement with an engagement feature of an anchor. The sliding knot 136 can be subsequently dressed or finalized as desired, including in manners described herein.

Figure 4:
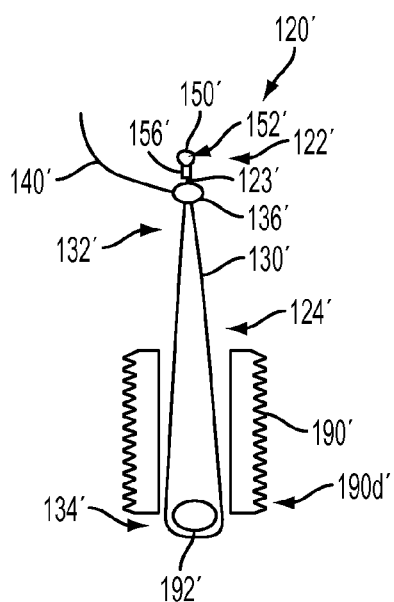
FIG. 4 is a schematic view of a filament coupled to an anchor from the surgical repair construct of FIG. 1.

FIG. 4 provides another exemplary embodiment of a filament 120' for use as part of a surgical repair construct. Similar to the filament 120, a first end 122' of the filament 120' can include a snare 150' having an opening 152' that is configured to collapse under tension, a second end 124' of the filament 120' can include a collapsible loop 130' that is configured to collapse under tension, independent of the snare 150', and a neck 123' can extend between the first and second ends 122', 124'. The filament 120' having both a snare 150' and a collapsible loop 130' can be referred to as a snare assembly.

The snare 150' can be formed in a variety of ways known to those skilled in the art, some of which are discussed in greater detail below. In the illustrated embodiment the snare 150' is formed by way of a sliding knot 156', such as, by way of non-limiting examples, a Buntline Hitch, a Tennessee Slider, a Duncan Loop, a Hangman's Noose, and a loop having a coaxial sliding neck. Although the type of sliding knot will affect the relative movement of the knot 156' and the filament 120' with respect to the direction either is moved to expand or collapse the snare 150', as described herein, unless otherwise designated, a knot used to form a snare is movable away from the second end 124' of the filament 120', i.e., away from the collapsible loop 130', to collapse the snare 150' and towards the second end 124', i.e., towards the collapsible loop 130', to increase a size of the snare 150'. A person skilled in the art would be able to adapt the teachings herein based on the type of sliding knot used in conjunction with the snare 150'.

Figure 5A:
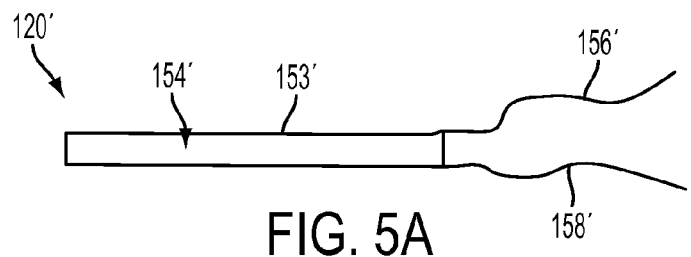
FIGS. 5A-5D are sequential views of one exemplary embodiment for forming a snare from a filament in which the snare has a coaxial sliding neck.
Figure 5B:
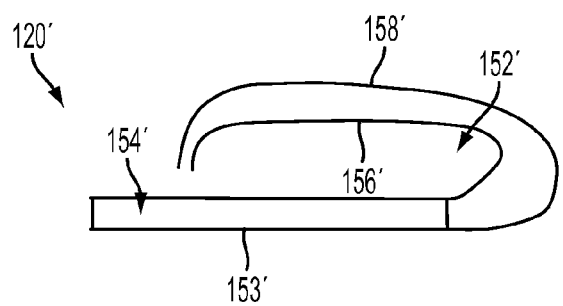
Figure 5C:
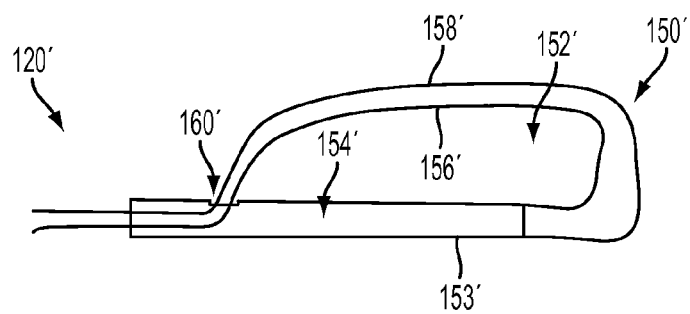
Figure 5D:
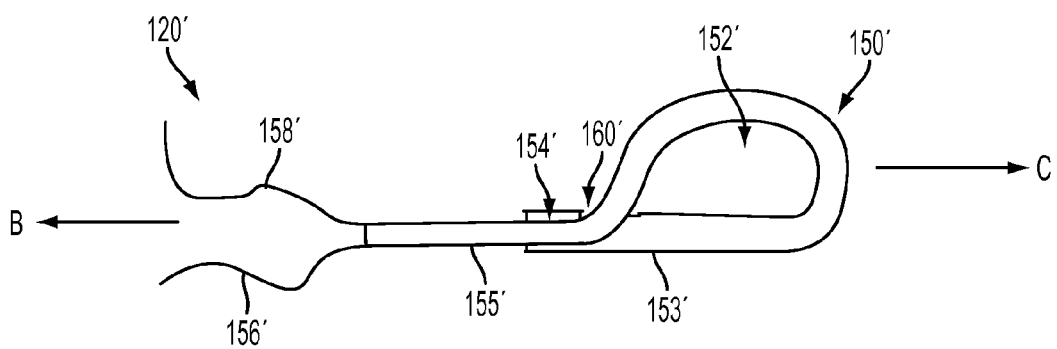

FIGS. 5A-5D illustrate one of the many ways the snare 150' can be formed. As shown, the snare 150' is formed from a bifurcated suture filament having a tubular portion 153' with a core removed therefrom to form a cannulated portion 154' and first and second terminal limbs 156', 158'. As shown in FIG. 5B, the terminal limbs 156', 158' can be curled back towards the tubular portion 153' to form a loop having an opening 152' that defines the snare 150'. As shown in FIG. 5C, a bore 160' can be formed on a side of the tubular portion 153' and the terminal limbs 156', 158' can be placed into the cannulated tubular portion 154' through the bore 160'. Ends of the terminal limbs 156', 158' can be fed through the cannulated portion 154', and as shown in FIG. 5D, the terminal limbs 156', 158' can be pulled distally (direction B in FIG. 5D) through the tubular portion 153' such that the tubular portion 153' is fed through itself and a coaxial sliding neck 155' that can slide with respect to the tubular portion 153' of the filament is formed. Accordingly, the snare 150' can be collapsed by tensioning the limbs 156', 158' and/or coaxial sliding neck 155' in approximately a first direction B, and the snare 150' can be expanded by applying a force to the snare 150' in approximately a second, opposite direction C, which pulls the limbs 156', 158' and the coaxial sliding neck 155' towards the snare 150'. Passing the filament through itself to form a coaxial sliding neck allows the filament to have a low profile that minimizes the amount of space the construct consumes in the body and that minimizes and/or eliminates trauma associated with passing the filament through tissue.

The loop 130' can likewise be formed in a variety of ways known to those skilled in the art, some of which are discussed in greater detail below. In the illustrated embodiment of FIG. 4, the loop 130' has first and second ends 132', 134' with a sliding knot 136' formed at the first end 132'. As shown, the second end 134' can be slidably coupled to an anchor 190', for instance at an engagement feature 192' thereof, such as a saddle or post. While in the illustrated embodiment the engagement feature 192' is located at a distal end 190d' of the anchor 190', it can be located in any part of the anchor 190' and allows the filament 120' to be slidably engaged with the anchor 190'.

The collapsible loop 130' can be expanded and collapsed as desired by the sliding knot 136' in a manner similar to as described with respect to the sliding knot 136 of the loop 130. Further, as shown in FIG. 4, the loop 130' can include a collapsible tail or tensioning limb 140' that extends from the sliding knot 136' and can operate in a manner similar to as described with respect to the tensioning limb 140. Thus, the loop 130' of the filament 120' can move in a ratchet-like or incremental fashion such that the knot 136' moves towards the second end 134' with little or no backlashing, which in turn minimizes or prevents the opening of the collapsible loop 130' from increasing in size. Still further, in some embodiments a second, stationary tail or tail can also be formed and used in a manner similar to as described with respect to the filament 120.

The filaments 120, 120' can be any suitable suture material such as a cannulated filament, a braided filament, and a mono filament. The type, size, and strength of the filament can depend, at least in part, on the other materials of the system, including the material(s) of any suture coupled thereto, any obstructions through which the filament may pass, and the type of procedure in which it is used. In one exemplary embodiment the filament is formed from a #0 filament (about 26 gauge to about 27 gauge), such as an Orthocord™ filament that is commercially available from DePuy Mitek, Inc or Ethibond™ filament available from Ethicon, Inc. Generally the filament is relatively thin to minimize any trauma to tissue through which it passes. In some embodiments the filament can have a size between about a #4 filament (about 21 gauge to about 22 gauge) and about a #4-0 filament (about 32 gauge to about 34 gauge). The Orthocord™ #2 filament can be useful because it has a braided configuration, which allows other components, including the filament itself and flexible members as discussed below, to pass through subcomponents of the braid without causing damage to the filament. Filaments configured to allow for a cannulated configuration, such as by removing a core therefrom or having a pre-formed cannulated configuration, can also be used. Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed.

A length of the filament can be in the range of about 2 centimeters to about 60 centimeters, and in one embodiment it can be about 40 centimeters. Still further, a diameter of the sliding knot of the loop will depend, at least in part, on the size of the filament used to form it, the type of sliding knot that it is, and the type of procedure with which it will be used. In one exemplary embodiment a diameter of the sliding knot of the loop can be in the range of about 0.5 millimeters to about 2 millimeters, and in one embodiment it can be about 1 millimeter. Likewise, if the snare is formed from a sliding knot, its diameter will also depend, at least in part, on the size of the filament used to form it, the type of sliding knot that it is, and the type of procedure with which it will be used.

Although in the embodiments described above the snare and collapsible loop are formed from the same filament, in other embodiments each component can be formed from a separate filament. Exemplary systems, devices, and methods related to such configurations involving the formation of snares and loops from a single filament or more than one filament are described at least in U.S. patent application Ser. No. 13/218,810 filed Aug. 26, 2011, and entitled "SURGICAL FILAMENT SNARE ASSEMBLIES," and in U.S. patent application Ser. No. 13/465,288 filed concurrently herewith, and entitled "Systems, Devices, and Methods for Securing Tissue", the content of each which is incorporated by reference herein in its entirety.

Figure 6:
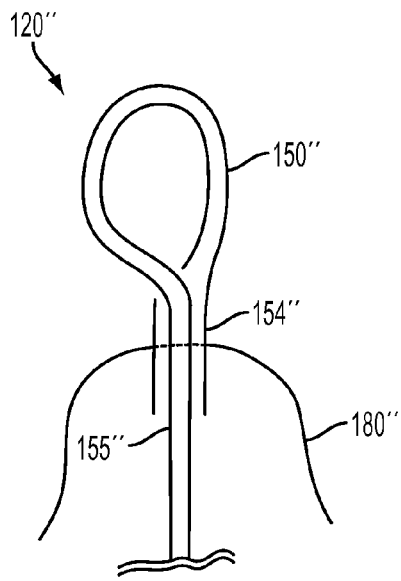
FIG. 6 is a schematic view of one exemplary embodiment of a snare formed from a filament and a flexible member in which the snare has a coaxial sliding neck and the flexible member is disposed through the snare.

Because the snare of the filament can both expand and contract, a flexible member, such as a suture pin, can be removably disposed across the neck to prevent unintentional movement of the snare. One exemplary embodiment of a flexible member 180" associated with a coaxially sliding neck 155" of a snare 150" of a filament 120" is shown in FIG. 6. As illustrated, the flexible member 180" can extend across the filament 120" to immobilize the coaxially sliding neck 155" with respect to a portion 154" of the filament 150" through which it is passed. When the surgeon desires to collapse the snare, the flexible member 180" can be removed. The use of a flexible member of the type described herein to prevent unintentional collapse of the snare in tissue repair procedures is advantageous as it can prevent unintentional collapse of the snare during the procedures, including in instances in which the snare is passed through obstructions, such as tissue.

Figure 7A:
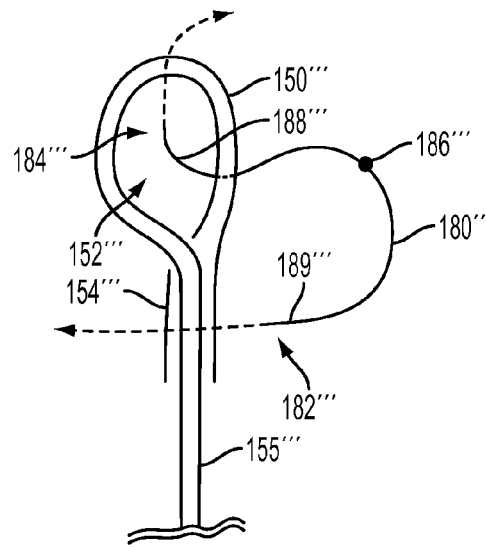
FIG. 7A is a schematic view of another exemplary embodiment of a snare formed from a filament and a flexible member in which the snare has a coaxial sliding neck, this view illustrating how the flexible member can be disposed through the neck and the snare.
Figure 7B:
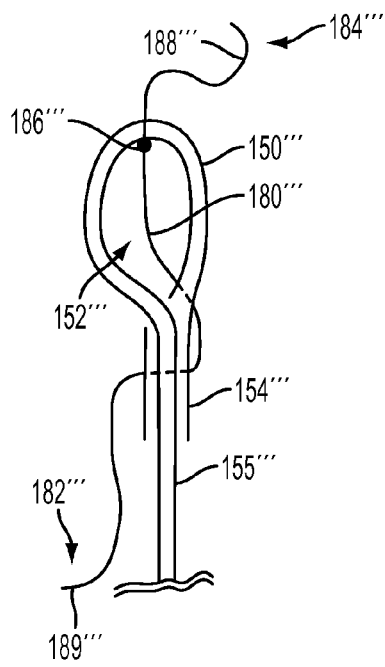
FIG. 7B is a schematic view of the snare and flexible member of FIG. 7A, illustrating the flexible member disposed through the neck and the snare.

In another embodiment, shown in FIGS. 7A and 7B, a flexible member 180''' can immobilize a snare 150''' of a filament and serve as a suture shuttle to guide the filament through obstructions, such as tissue, during the course of a procedure. As shown in FIG. 7A, a first end 182''' of the flexible member 180''' can be passed across the filament, including a cannulated portion 154''' and a coaxially sliding neck 155''' of the filament, so that a first portion of the flexible member 180''' is disposed through the coaxially sliding neck 155''', while a second end 184''' of the flexible member 180''' is passed through and disposed in the snare 150'''. A protrusion 186''', for instance a stationary knot that can be pre-formed or formed or modified during a procedure, can be disposed on the flexible member 180''' at a location between the first and second ends 182''', 184'''. The protrusion 186''' can serve to maintain the flexible member 180''' in a coupled arrangement with the filament, and as shown in FIG. 7B, the protrusion 186''' can be disposed within the opening or loop 152''' formed by the snare 150''', abutting a surface of the snare, with a terminal portion 188''' extending through and beyond the loop 152''' for use as a shuttle. Optionally, a needle or similar tool or device can be coupled to the terminal portion 188''' to assist in threading the filament 120''' through tissue.

Other configurations in which a flexible member is used as both a suture pin and a suture shuttle are also possible, depending, at least in part, on the configuration of the filament and obstructions though which the filament will be passed, without departing from the spirit of the present disclosure. For example, the flexible member 180''' can be disposed through another portion of the coaxially sliding neck 155''' or a different portion of the snare 150'''. One benefit of using a flexible member for both maintaining a snare shape and shuttling the filament is that it can improve filament management by limiting the number of filaments used in a procedure. Further, such a construction allows for a single action to remove both the pin and the shuttle from the filament, such as by grabbing the flexible member 180''' between the stationary knot and the coaxially sliding neck 155''' to decouple the flexible member 180''' from the filament. In still other embodiments a flexible member can be used primarily for the purpose of shuttling the filament and/or one flexible member can be used as a suture pin and a second flexible member can be used as a suture shuttle.

The flexible member(s) can be made of a variety of materials, but in one exemplary embodiment it is a surgical filament that is separate from the filament that forms the snare and collapsible loop. In some embodiments the flexible member is formed using a surgical filament, such as a cannulated filament, a braided filament, and a mono filament. The type, size, and strength of the filament can depend, at least in part, on the other materials of the system, including the material(s) of the filament through which it will pass, the obstructions through which the snare will pass, how the filament is being used (e.g., as a suture pin, as a suture shuttle, or as a joint suture pin and suture shuttle), and the type of procedure in which it is used. In one exemplary embodiment the flexible member is formed from a #2-0 filament (about 28 gauge), such as an Orthocord™ filament that is commercially available from DePuy Mitek, Inc. or Ethibond™ filament available from Ethicon Inc. Generally the flexible member is relatively thin to minimize any trauma to tissue through which it passes, and typically the flexible member is thinner than filament through which it passes. In some embodiments the flexible member can have a size between about a #1 filament (about 25 gauge to about 26 gauge) and about a #6-0 filament (about 38 gauge to about 40 gauge). A length of the flexible member can be in the range of about 1 centimeter to about 100 centimeters. In one embodiment in which the flexible member is only being used as a suture pin it can have a length of about 2 centimeters. In one embodiment in which the flexible member is used as both a suture pin and a suture shuttle it can have a length of about 100 centimeters.

Figure 8:
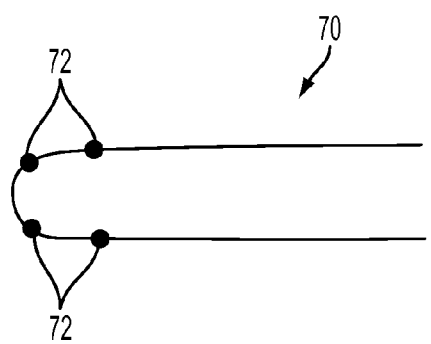
FIG. 8 is a schematic view of a suture from the surgical repair construct of FIG. 1.

FIG. 8 illustrates one exemplary embodiment of a suture 70 for use as part of the surgical repair construct 10. The suture is generally a flexible member having one or more stationary protrusions 72 formed therein. The protrusions 72 can have a spaced-apart arrangement, can be pre-formed by the suture manufacturer, or alternatively, a surgeon can form one or more of the protrusions 72 in advance of or during a surgical procedure. Different spaced-apart arrangements can be used for different procedures with the spaced-apart relationship being based, at least in part, on the other components of the surgical repair construct 10, the tissue(s) that will be coupled to the suture 70, and the type of procedure being performed. In the illustrated embodiment, there are four protrusions 72 approximately equidistant from each other, although any number of protrusions, including by way of non-limiting example six, in any form of spaced relationships can be used. The protrusions 72 can be used to assist in grasping soft tissue for repair to help prevent the collapsed snare 50 of the filament 20 from backlashing and to provide additional strength to the tissue-to-bone attachment.

One skilled in the art will appreciate that protrusions 72 can be formed by placing a knot in the suture 70, or by affixing another object to the suture 70.

The suture can be made of any suitable suture material, such as a cannulated filament, a braided filament, and a mono filament. The type, size, and strength of the filament can depend, at least in part, on the other materials of the system, including the material(s) of the filament with which it will be coupled, the tissue(s) through which the suture may pass, and the type of procedure in which it is used. In one exemplary embodiment the suture is formed from a size #2 (23-24 gauge) filament, such as an Orthocord™ filament that is commercially available from DePuy Mitek, Inc. or Ethibond™ filament available from Ethicon, Inc. Generally the suture is relatively thin to minimize any trauma to tissue through which it passes. In some embodiments the suture can have a size between about a #5 filament (about 20 gauge) and about a #4-0 filament (about 32 gauge to about 34 gauge). A length of the suture can be in the range of about 10 centimeters to about 120 centimeters, and in one embodiment the suture has a length of about 90 centimeters. Still further, a diameter of the protrusions can be in the range of about 0.5 millimeters to about 2 millimeters, and in one embodiment the diameter of each of the protrusions is about 1 millimeter. Additionally, a length of a space between each of the protrusions can be in the range of about 1 millimeter to about 10 millimeters, and in one embodiment the length of the space between each protrusion is about 5 millimeters. The diameters of the protrusions along a length of the suture and a length of a space between each of the protrusions can all be the same, or they can vary from protrusion to protrusion.

One exemplary method for performing a rotator cuff repair using the repair construct 10 illustrated in FIG. 1 is schematically illustrated in FIGS. 9A-9E. A surgical opening can be formed through skin 104 and a cannula can be passed therethrough to create a surgical repair site in a manner well known to those skilled in the art. Although cannulas are often used to define a channel through which the procedure can be performed, the cannula is not shown in FIGS. 9A-9E for ease of illustration. Accordingly, to the extent the figures show components of the systems and devices passing through skin 104, these components would typically be extending through the cannula, which itself is passed through the skin 104. Further, although the devices and methods described herein are particularly useful for minimally invasive surgery, such as arthroscopic surgery, they can also be used in open surgical procedures.

Figure 9A:
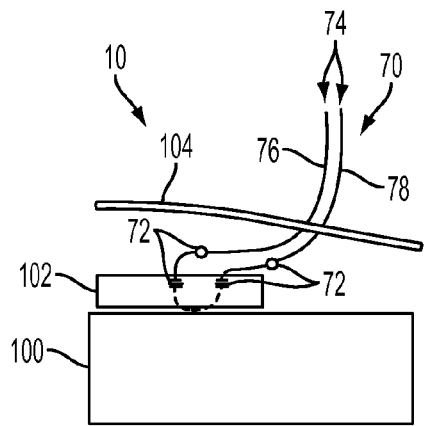
FIGS. 9A-9E are sequential views of one exemplary embodiment for using the surgical repair construct of FIG. 1 to secure tissue to bone.

As shown in FIG. 9A, the suture 70 can be passed through a tendon 102 detached from bone 100 such that at least one of the protrusions 72 is disposed adjacent to at least one side of the tendon 102. In the illustrated embodiment, two protrusions 72 are located proximal of the tendon 102 while two protrusions 72 are disposed within the tendon 102. Although not shown, it is understood that one or more protrusions can be formed on the distal side of the tendon 102, as opposed to within it. The suture 70 can be passed completely or partially through the tissue using any number of techniques known to those skilled in the art, including by coupling a needle or similar tool or device to one of terminal ends 74 of the suture 70 to assist with threading the suture 70 through the tendon 102. In one exemplary embodiment, one of the terminal ends 74 is passed through the tendon 102 from a first (proximal) side of the tendon 102 facing away from the adjacent bone 100 and back through the tissue from a second (distal) side of the tendon 102 facing towards the bone 100 such that first and second limbs 76, 78 of the suture 70 extend from the first side of the tendon 102, i.e., proximal of the tendon 102. The suture 70 can be manipulated by a surgeon with respect to the tendon 102 to expose as many protrusions 72 as desired. Protrusions 72 located proximal of and adjacent to the tendon 102 can be used to help maintain a location of the collapsed snare 50 as well as to accommodate variations in tissue thickness and the bite size (i.e., the distance between the locations that the suture limbs enter the tissue). In one embodiment it is particularly useful to have at least two fully-exposed protrusions in close proximity to the tendon 102. A person skilled in the art will recognize that there are other ways by which the suture 70 can be coupled to or shuttled through the tendon 102, including, by way of non-limiting example, by wrapping the suture 70 around the tendon 102 such that at least one of the protrusions 72 is proximal of the tendon 102. Further, the suture can be passed through tissue (e.g., tendon 102) through a variety of techniques and orientations known to those skilled in the art.

Figure 9B:
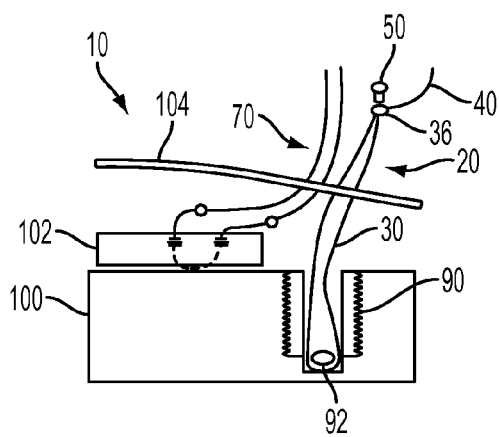

As shown in FIG. 9B, the anchor 90 can be fixated into bone 100 using ordinary techniques, such as with a driver to screw or tap the anchor 90 into place. In the illustrated embodiment the filament 20 is already coupled thereto at the engagement feature 92, although in other embodiments the filament 20 can be slidingly coupled to the anchor 90 after the anchor 90 is positioned at its desired location. As shown, the filament 20 includes the snare 50, the collapsible loop 30, the sliding knot 36, and the collapsible tail or tensioning limb 40.

Figure 9C:
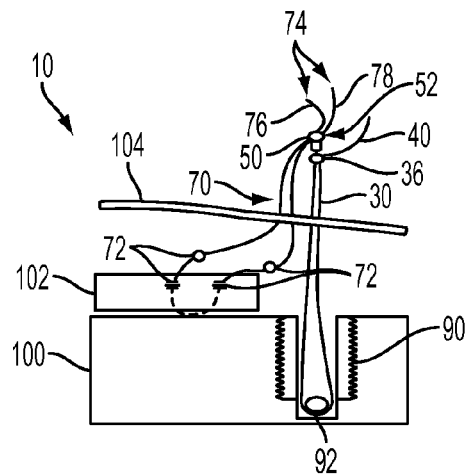
Figure 9D:
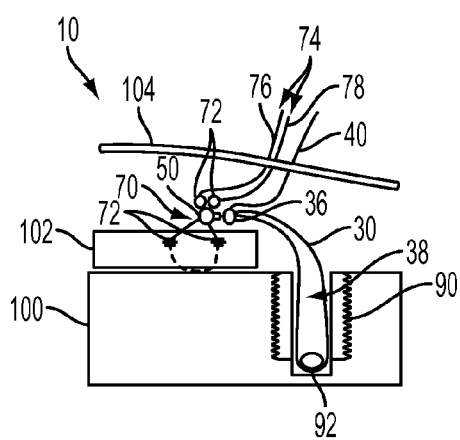

As shown in FIG. 9C, the terminal ends 74 of the first and second limbs 76, 78 of suture 70 can be passed through the opening 52 of the snare 50, thereby placing the tendon 102 in a position to be coupled to the filament 20. The snare 50 can then be advanced distally towards the bone 100, for instance by sliding the snare 50 along the suture 70, until the snare 50 is distal of at least one of the protrusions 72 and proximal of the tendon 102. As shown in FIG. 9D, the snare 50 can be advanced distal of two protrusions 72 and is located approximately adjacent to the tendon 102. In other embodiments the snare 50 can be advanced distal of three or more protrusions 72. Any number of techniques known to those skilled in the art can be used to advance the snare 50 distally, including using a pusher tool or advancing it by hand.

After the snare 50 has been advanced distally past at least one of the protrusions 72 and to its desired location, the snare 50 can be collapsed or dressed in a manner consistent with its snare type. Collapsing the snare 50 around the suture couples the tendon 102 to the filament 20 and directs it towards the bone 100. In some embodiments, a flexible member can be disposed through the snare 50 to prevent unintentional collapse of the snare opening 52. In such embodiments, the flexible member can be removed prior to collapsing or dressing the snare. Further, although in the illustrated embodiment the snare 50 is collapsed after it is advanced distally past at least one of the protrusions 72, in other embodiments the snare 50 can be at least partially collapsed prior to fully advancing it in the distal direction provided that the opening 52 in the snare 50 is still configured to allow at least one of the protrusions 72 to pass therethrough.

Figure 9E:
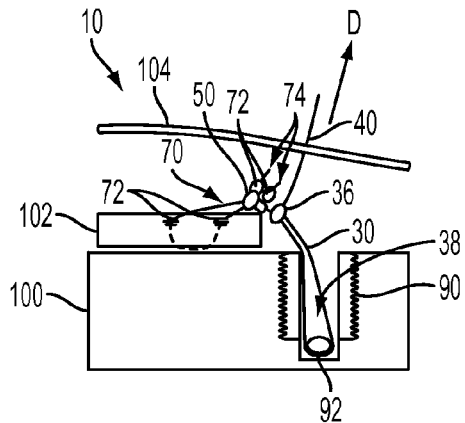

As shown in FIG. 9E, tension can be applied to the tensioning limb 40 by pulling approximately in a direction D, thereby causing the sliding knot 36 to advance distally towards the bone 100 to decrease a size of the opening 38 of the collapsible loop 30, i.e., shorten the collapsible loop 30. This movement also applies additional tension to the suture 70 by virtue of being coupled to the filament 20, and in turn brings the tendon 102 into proximity with the bone 100. The configuration of the filament 20 in conjunction with the suture 70 allows the knot 36 to be advanced in an incremental, ratchet-like fashion when the tensioning limb 40 is pulled in the direction D without the risk of reversing the progress of the knot 36 as a result of slipping backward, sometimes referred to as backing out, backlashing, or slackening of the filament. Optionally, as shown, excess portions of the terminal ends 74 of the suture 70 proximal of the protrusions 72 can be cut-off and removed. Likewise, an excess portion of the tensioning limb 40 can also be cut-off and removed if desired. In embodiments in which the filament includes a stationary terminal tail or limb adjacent to the tensioning limb, excess portions of that limb can likewise be cut-off and removed if desired. Still further, optionally, one or more half-hitches can be added to the filament 20, for instance on the tensioning limb 40, the suture 70, or a stationary terminal limb if such limb exists, to provide additional strength once the filament 20 and suture 70 have been finally positioned to approximate tissue. Other than the optional half-hitches, no knots need to be tied during the course of the illustrated procedure.

The resulting break strength of the formed attachment can be in the range of about 50 Newtons to about 200 Newtons without the formation of any half-hitches, and in one embodiment the break strength can be about 130 Newtons without the formation of any half-hitches. The use of half-hitches typically increases the load capacity.

The procedure discussed with respect to FIGS. 9A-9E is just one example of a procedure that can be performed in conjunction with systems, devices, and methods disclosed herein. A person skilled in the art will recognize a number of other ways that the disclosed systems, devices, and methods can be used in various other configurations and types of surgical procedures. For example, although the filament 20 of FIGS. 9A-9E is coupled to an anchor, in other embodiments, no anchor can be used and instead repair constructs of the nature disclosed herein can be coupled directly to bone without an anchor. Alternatively, repair constructs of the nature disclosed herein can be used to draw two or more tissues together by passing a filament of a construct through one tissue, a suture having one or more stationary protrusions formed thereon through a second tissue, and the operating the construct in a manner consistent with the teachings herein. Further, the systems, devices, and methods can easily be adapted to be used in conjunction with three or more components, such as multiple tissues and a bone or three or more soft tissue components. Some non-limiting examples of other systems, devices, assemblies, constructs, and surgical procedures with which the present systems, devices, and methods can be used are described in U.S. patent application Ser. No. 13/218,810 filed Aug. 26, 2011, and entitled "SURGICAL FILAMENT SNARE ASSEMBLIES," and in U.S. patent application Ser. No. 13/465,288 filed concurrently herewith, and entitled "Systems, Devices, and Methods for Securing Tissue", the content of which was previously incorporated by reference herein in their entireties.

One skilled in the art will appreciate further features and advantages of the invention based on the above-described embodiments. Accordingly, the invention is not to be limited by what has been particularly shown and described, except as indicated by the appended claims. By way of non-limiting example, although the embodiments described herein include a snare formed in a first end of the filament, other components having similar functionality can be associated with the first end of the filament, such as a clip or a like element to clamp a portion of the suture. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A surgical repair method, comprising:
   passing through detached soft tissue a first end of a suture having formed thereon a plurality of stationary protrusions, the first end of the suture being passed through the tissue such that first and second limbs of the suture extend from the first side of the tissue, the suture being arranged in tissue such that at least one of the protrusions is disposed adjacent to at least one of the first and second sides of the tissue;
   inserting an anchor into bone in proximity to detached soft tissue, the anchor having attached to a filament engagement feature thereof a filament, the filament having a collapsible snare formed on one end thereof and a collapsible loop at a second end thereof and coupled to the filament engagement feature, the collapsible loop including a sliding knot with a tensioning limb extending therefrom and effective to collapse the collapsible loop independent of the snare;
   inserting the first and second limbs of the suture through an opening formed in the snare;
   sliding the snare distally towards the tissue and distally past at least one protrusion disposed on the first side of the tissue;
   collapsing the snare around the first and second limbs of the suture; and
   pulling the snare towards the anchor by shortening the collapsible loop and drawing the tissue into proximity with the bone.

2. The method of claim 1, wherein the step of pulling the snare towards the anchor by shortening the collapsible loop comprises tensioning the tensioning limb.

3. The method of claim 2, wherein the snare is advanced in an incremental fashion without slackening of the filament.

4. The method of claim 1, wherein the suture includes at least four protrusions.

5. The method of claim 4, wherein the snare is positioned between at least one protrusion and the tissue.

6. The method of claim 4, wherein the snare is positioned between at least two protrusions and the tissue.

7. The method of claim 1, wherein a flexible member is disposed in a portion of the snare to prevent unintentional collapse thereof, the method further comprising removing the flexible member from the snare prior to collapsing the snare.

8. The method of claim 1, wherein the method is performed without tying a knot.

* * * * *